(12) United States Patent
Dubois et al.

(10) Patent No.: US 9,365,478 B2
(45) Date of Patent: Jun. 14, 2016

(54) METHOD FOR DIRECTLY SYNTHESIZING UNSATURATED ALDEHYDES FROM ALCOHOL MIXTURES

(71) Applicants: Jean-Luc Dubois, Millery (FR); Mickaël Capron, Bachy (FR); Franck Dumeignil, Fretin (FR)

(72) Inventors: Jean-Luc Dubois, Millery (FR); Mickaël Capron, Bachy (FR); Franck Dumeignil, Fretin (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/437,565

(22) PCT Filed: Oct. 17, 2013

(86) PCT No.: PCT/FR2013/052477
§ 371 (c)(1),
(2) Date: Apr. 22, 2015

(87) PCT Pub. No.: WO2014/068213
PCT Pub. Date: May 8, 2014

(65) Prior Publication Data
US 2015/0266800 A1 Sep. 24, 2015

(30) Foreign Application Priority Data

Oct. 29, 2012 (FR) ...................... 12 60298

(51) Int. Cl.
*C07C 45/38* (2006.01)
*C07C 45/75* (2006.01)

(52) U.S. Cl.
CPC ................ *C07C 45/38* (2013.01); *C07C 45/75* (2013.01)

(58) Field of Classification Search
None
See application file for complete search history.

(56) References Cited

U.S. PATENT DOCUMENTS 7,759,525 B2 * 7/2010 Dubois ............... B01J 23/002
568/593

FOREIGN PATENT DOCUMENTS

| GB | 513772 | 10/1939 |
| WO | 2005/040392 A1 | 5/2005 |
| WO | 2011/083225 A1 | 7/2011 |
| WO | 2011/093763 A1 | 8/2011 |

OTHER PUBLICATIONS

International Search Report for PCT/FR2013/052477, dated Jan. 27, 2014.
Blom, C.E., et al., "Molecular Structure of s-cis- and s-trans-Acrolein Determined by Microwave Spectroscopy", *J. Am.Chem. Soc.*, vol. 106 (1984), pp. 7427-7431.
Soares, Ana Paula Vieira et al., "Methanol Selective Oxidation to Formaldehyde over Iron-Molybdate Catalysts", *Catalysis Reviews*, vol. 47 (2004), pp. 125-174.
Twigg, Martyn V., "Catalyst Handbook", Second Edition, Wolfe Publishing Ltd., (1989), pp. 490-503.

* cited by examiner

*Primary Examiner* — Brian J Davis
(74) *Attorney, Agent, or Firm* — Brinks Gilson & Lione

(57) ABSTRACT

The present invention concerns a method for directly synthesizing acrolein or methacrolein from a mixture of methanol and ethanol or propanol. The method of the invention comprises two successive phases: oxidation in the presence of a selective oxidation catalyst of the light alcohols of the feedstock, then condensation by aldolization of the aldehydes formed during oxidation in the presence of a condensation catalyst (aldolization). Alternatively, the two phases can be carried out in the presence of a single catalyst, in particular in the presence of a molybdenum-based selective oxidation catalyst. These two phases can be conducted in a single reactor or in two cascade reactors.

14 Claims, No Drawings

METHOD FOR DIRECTLY SYNTHESIZING UNSATURATED ALDEHYDES FROM ALCOHOL MIXTURES

This application is a National Stage Application of International Application No. PCT/FR2013/052477, filed Oct. 17, 2013. This application also claims priority under 35 U.S.C. § 119 to French Patent Application No. 1260298, filed Oct. 29, 2012.

A subject of the present invention is a process for the direct synthesis of acrolein or methacrolein from a mixture of methanol and ethanol or propanol.

Acrolein is the usual name given to the unsaturated aldehyde of formula $CH_2=CH-CHO$ known as propenal, and methacrolein is the name given to the compound $CH_2=C(CH_3)-CHO$, or 2-methylpropenal.

Acrolein has been known for a very long time and is used as a broad-spectrum biocide; it is also an intermediate in the synthesis of a wide range of products, such as D,L-methionine (a supplement for animal feed), acrylic acid, pharmaceutical products, fungicides, perfumes, pyridine, picolines, glutaraldehyde, etc.

Methacrolein has also been known for a very long time and is essentially used, notably, for the synthesis of methacrylic acid and methyl methacrylate and also for the synthesis of synthetic resins and polymers.

At present, the main industrial processes known for the manufacture of acrolein are the process developed by DEGUSSA during the 1940s, using acetaldehyde and formaldehyde as starting materials, and the process established some 20 years later by several companies and consisting of the oxidation of propylene. In more recent years, a process for producing acrolein by dehydration of glycerol has been developed by the applicant company.

The DEGUSSA process, which is illustrated by the patent UK 513,772, filed on Mar. 31, 1938 with priority of Apr. 1, 1937, and by the paper entitled "Synthese und Umwandlungsprodukte des Acroleins" [Synthesis and conversion products of acrolein] in Angewandte Chemie, Vol. 62, No. 5, pages 105-132, published on Mar. 7, 1950, and is carried out in the gas phase by heterogeneous catalysis, is based on the following aldol reaction:

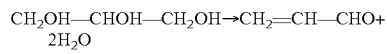

The paper in the *Journal of the American Chemical Society*, 1984, 106, pp. 7427-7431, describes conditions for synthesizing an acrolein $^{13}C$ isotope by an aldol reaction of formaldehyde with acetaldehyde which was formed by the oxidation of ethanol ($^{13}C$).

The second process, which is illustrated in Techniques de l'Ingénieur [Techniques of the Engineer], in the document relating to "Génie des precédés" [Process Engineering] J6 100, pages 1 to 4, has replaced the previous process, industrially speaking, and is based on the following reaction for the oxidation of propylene:

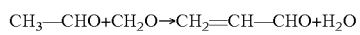

said process using mixed oxide catalysts based on molybdenum, bismuth and iron described in "Precédés de Pétrochimie" [Petrochemical Processes], A. Chauvel, G. Lefebvre and L. Castex, Volume 2, Editions Technip, 2nd Edition, 1986, pages 213-219; such a process is also described in the catalysis sheet 34 from the Catalysis Division of the Société Française de Chimie [French Chemical Society].

More recently, considerable work has been carried out by the applicant company (see patent application WO 2011/083225) to develop another synthesis process starting from glycerol which is subjected to dehydration according to the following reaction:

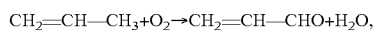

This type of process affords the advantage of being able to work with a natural, renewable (non-fossil) starting material and hence of fulfilling the commitments made by most industrialized countries targeted at reducing greenhouse gas emissions and the environmental impact thereof, and also of enabling a more sustainable production solution to be attained.

Methacrolein synthesis generally uses isobutane, terf-butanol or isobutene as starting materials, which are converted by oxidation to acrolein. There are other synthesis processes, such as oxydehydrogenation of isobutyraldehyde or hydroformylation of methylacetylene or propadiene. As well as in some cases their cost, the fossil origin of these starting materials is a major shortcoming.

As has been seen, these various processes have drawbacks.

Industrial processes based on oxidation of olefins consume fossil starting materials, extracted in particular from oil, the acquisition cost of which is becoming ever higher. Moreover, their availability is linked to refineries or petrochemical plants having high capacities, in practice necessitating setting up close to large petrochemical sites, thus entailing costs of transporting to the end consumer, not to mention the risks of emitting pollutants.

Processes implementing the aldol reaction entail significant capital costs insofar as, if it is desired to dispense with the purchase of starting materials—formaldehyde and acetaldehyde, which are not readily stored or transported; for example formaldehyde may only be transported within a radius of 400 km around the production site, and for this transportation must be stabilized with methanol in aqueous solution—it is necessary to provide specific plants for synthesizing these products, which adds to the cost of the aldol reaction plant proper. Acetaldehyde synthesis is generally carried out by the Wacker reaction for the oxidation of ethylene, and formaldehyde synthesis is generally carried out by oxidation (or oxydehydrogenation, depending on the catalytic system used) of methanol.

Processes implementing the dehydration of glycerol are attractive due to the renewable nature of the feedstock treated. However, they have some drawbacks at several levels. Indeed, supplying glycerol depends mainly on oleochemical and/or biodiesel plants. Glycerol is only available in limited quantities which in practice restricts the possible size of the acrolein production plants and hence their economic profitability. The most widespread grades of glycerol are those known as crude glycerol, which commonly corresponds to 80% by weight aqueous glycerol solutions containing salts (for example $NaCl$, $KCl$, $Na_2SO_4$, $K_2SO_4$, etc.), residual methanol when it has been obtained through methanolysis of vegetable oils, Matter Organic Non-Glycerol (MONG), and all kinds of impurities extracted from plants or animal fats during the production processes. These impurities are catalyst poisons and lead to reversible deactivation, for example by coke formation, or irreversible deactivation, for example by salt deposition. Refined glycerol is also available commercially, but at much higher prices. From a technical standpoint, dehydration catalysts known to date deactivate quickly, which entails regular regenerations, meaning an additional capital cost (for example doubling or tripling the volumes of catalyst). Finally, this "green" process has a drawback in that the dehydration reaction, which is carried out in the gas phase and is overall highly energy-consuming, is dependent on the cost of this energy, currently provided by fossil fuels, which also necessarily impact on the environment.

The applicant company has thus sought a process which alleviates the above drawbacks, that is to say which uses starting materials of renewable (non-fossil) origin and which limits capital costs as far as possible. Thus, the applicant company has discovered that it is possible to directly synthesize acrolein and methacrolein using a mixture of methanol and ethanol (for acrolein) or methanol and propanol (for methacrolein) as feedstock, which compounds are available from renewable starting materials.

In the document *Journal of the Chemical Society, Chemical Communications,* 1991, 1760-1761, a mixture of methanol and ethanol is converted into a mixture comprising acrolein, acetaldehyde and isobutyraldehyde in the presence of a V/TiO$_2$ catalyst. There is no oxygen in the reaction medium and the process predominantly leads to the formation of saturated aldehydes, such as isobutyraldehyde.

Example 32 in application WO 2005/040392 describes the oxidation of a mixture of methanol and ethanol in the presence of a silver catalyst, giving a mixture of acetaldehyde and formaldehyde which is then converted into acrolein in the presence of alumina. This example uses a reaction mixture with an unspecified composition and requires the reaction temperature to be adapted at each of the stages.

The applicant company has now discovered a simplified process for synthesizing acrolein from a mixture of methanol and ethanol, in that it is carried out directly, in the presence of a solid selective oxidation catalyst and optionally of a solid aldol condensation catalyst.

The applicant company has also found that this process applies to the synthesis of methacrolein from a mixture of methanol and propanol.

Within the meaning of the invention, "directly" is understood to mean a process carried out in just one reaction system. This reaction system comprises either a single reactor or two successive reactors but, in the latter case, the second reactor is supplied, preferably directly, by the outlet effluent from the first reactor.

A subject of the invention is a process for the direct synthesis of unsaturated aldehydes of formula CH$_2$=C(R)—CHO, in which R represents H or CH$_3$, from a feedstock containing a mixture of methanol and a second alcohol of formula R—CH$_2$—CH$_2$OH, consisting in introducing, into a reaction system operated in the gas phase at a temperature of between 200 and 400° C. and under a pressure of between 1 and 10 bar absolute and containing a solid selective oxidation catalyst chosen from molybdenum-based catalysts and optionally a solid aldol condensation catalyst, a feedstock containing the mixture of the two alcohols with oxygen and an unreactive diluent gas, such that the alcohol mixture and the oxygen each represent at most 10% of the total volume of the reaction mixture, and then, at the outlet of the reaction system, in recovering the gaseous effluent comprising the unsaturated aldehyde formed, in the presence of water coproduced by the reaction.

The process of the invention consists in synthesizing the two aldehydes of formulae HCHO and R—CH$_2$—CHO simultaneously in a first phase by oxidation of the alcohols on contact with the oxidation catalyst, then in carrying out a cross-condensation (aldol) reaction of these two aldehydes on contact with the condensation catalyst in a second phase, leading to the formation of an aldol of formula CH$_2$OH—CH(R)—CHO, which, by catalytic dehydration, gives the unsaturated aldehyde.

The applicant company has discovered, surprisingly, that the two phases, namely the two successive reactions of oxidation and of aldol reaction, may be carried out in the presence of a single catalyst, notably in the presence of a molybdenum-based selective oxidation catalyst.

Thus, in the process of the invention, a molybdenum-based catalyst for the selective oxidation of the light alcohols of the feedstock is used, and optionally a catalyst for the condensation (aldol reaction) of the aldehydes formed during the oxidation is used.

Catalysts for the selective oxidation of light alcohols have been well known for decades. Two main processes for the oxidation of light alcohols are known: i) the "silver-catalyzed" process in which the oxidation, or rather the dehydration, is carried out at high temperature, around 600 to 700° C., as described in The Catalyst Handbook, M. V. Twigg, published by Wolfe Publishing Ltd (1989), Chapter 10: Catalytic Oxidations. Methanol Oxidation. 10.3.2, pages 490-499; and ii) a process implementing a solid molybdenum-based mixed oxide-type oxidation catalyst described in the same handbook on pages 499-503, which process is carried out at a markedly lower temperature, between 300 and 400° C., with catalysts analogous to those used in the FORMOX process.

In the process of the invention, a solid molybdenum-based mixed oxide-type oxidation catalyst is used.

The oxidation catalysts which may be used in the process of the invention comprise molybdenum and at least one element chosen from P, Si, W, Ti, V, Nb, Ta, Cr, Mn, Fe, Co, Ni, Cu, Zn, Ga, In, Tl, Sb, Ag, As, Ge, B, Bi, La, Ba, Sb, Te, Ce, Pb, chosen from the group consisting of mixed oxides containing molybdenum and heteropolyacids containing molybdenum.

These catalysts may be represented by the following general formula:

in which:

A is at least one cation chosen from the elements of Groups 1 to 16 of the Periodic Table of the Elements and the lanthanides, preferably a cation of an alkali metal such as Cs, Rb or K, X is P or Si, and is preferably P, Z is at least one element chosen from the group consisting of W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb and is preferably Cu, Fe, Bi, Co, Ni, W, V, Cr, Sb, Mn or Ce, O is oxygen, a, b, c and d are indices consisting of integers or decimals corresponding to the following ranges:

$0 \leq a \leq 9$ and preferably $0 < a \leq 9$
$0 \leq b \leq 2$ and preferably $0.1 \leq b \leq 1.5$
$0 < c \leq 12$ and preferably $5 < c \leq 12$
$0 \leq d \leq 12$ and preferably $0 < d \leq 4$
such that a+b+d>0, and e is a number determined by the total degree of oxidation of the elements.

The catalyst used during this oxidation step may be a catalyst of the doped or undoped Fe—Mo—O type generally used during the oxidation of methanol to formaldehyde. Examples of iron molybdate (Fe—Mo—O) catalysts are described in *Catalysis Review*, Vol. 47 (2005), pp 125-174. These catalysts are available commercially. Mapco, for example, supplies a catalyst with its technology license, and Süd Chemie supplies several grades of these catalysts under the brand name FAMAX®: FAMAX J5, FAMAX MS, FAMAX HS, FAMAX TH. In the case of this type of Fe—Mo catalyst, the value of the indices a and b of the general formula above will preferably be 0 and the value of the index d will not be 0.

Preferably, notably in the process variant which uses a single catalyst, the oxidation catalyst is a catalyst of iron molybdate type.

The oxidation catalysts may be in bulk form and in this case used without support.

The catalysts may also be deposited on an inactive support, the quantity of which represents from 30 to 90% and preferably at least 50% of the total weight of the catalyst.

It is possible to use any material, such as steatite, silica, alumina, magnesia, titanium oxide, zirconia, silicon carbide, silicates, diatomaceous earths, borates or carbonates, or ceramics, as support, as long as the materials are stable to the operating conditions to which the catalysts are subjected.

The bulk catalyst or the supported catalyst may be in granular or powder form and may have any shape whatsoever, such as a sphere, grain, hollow cylinder, trilobe, quadrilobe, and also the shape of extruded or compressed cylinders, optionally by using a pelleting agent. Preferably, the catalyst has the shape of hollow cylinders or hollow trilobes.

In the process of the invention, use may be made of any solid catalyst known in the literature for carrying out the condensation of two aldehydes and notably of formaldehyde with a higher aldehyde (acetaldehyde or propisnaldehyde) to give the corresponding unsaturated aldehyde in two steps: aldol reaction of formaldehyde with the higher aldehyde to form a hydroxylated aldehyde (aldol), followed by a dehydration reaction of this aldol.

The condensation catalysts used in the process of the invention belong to the following different categories:

1) "Supported bases", that is to say alkali metal hydroxides LiOH, NaOH, KOH, CsOH deposited on a silica or alumina support, alkali metals and alkaline earth metals dispersed on silica, alumina ($Al_2O_3$—NaOH—Na), magnesia (MgO—NaOH), charcoal or potassium carbonate, nitrogenous compounds $NR_3$, $NH_3$, $KNH_2$ deposited on alumina, $LiCO_3$ deposited on silica, t-BuOK deposited on xonotlite and more generally solids of alkali metal type deposited on alumina (such as $Na/Al_2O_3$ or $KF/Al_2O_3$), on silica or on magnesia (such as Li/MgO).

This solid catalyst will consist, for example, of sodium silicate deposited on silica or on aluminosilicate preferably having an Si/Al atomic ratio of greater than 10 and comprising, where appropriate, a metal promoter or else cesium deposited on silica grafted with or doped by a zirconium compound ($Cs$—$Zr/SiO_2$).

2) "Metal oxides" BaO, BeO, SrO, CaO, $Al_2O_3$, $Y_2O_3$, $La_2O_3$, $CeO_2$, $ThO_2$, $SnO_2$, $K_2O$, $Na_2O$, MgO, ZnO, $TiO_2$, $ZrO_2$ in oxide or carbonate form optionally doped with an alkali metal, oxides or oxycarbonates of rare earth metals optionally doped with alkali metals.

3) "Metal salts" of the above compounds, that is to say carbonates, hydroxycarbonates, bicarbonates, ammonium salts, etc.

4) "Mixed oxides", such as $SiO_2$—MgO, $SiO_2$—CaO, $SiO_2$—SrO, $SiO_2$—BaO, $SiO_2$—SnO, $SiO_2$—ZnO, $SiO_2$—$Al_2O_3$, $SiO_2$—$ThO_2$, $SiO_2$—$TiO_2$, $SiO_2$—$ZrO_2$, $SiO_2$—$MoO_3$, $SiO_2$—$WO_3$, $Al_2O_3$—MgO, $Al_2O_3$—$ThO_2$, $Al_2O_3$—$TiO_2$, $Al_2O_3$—$ZrO_2$, $Al_2O_3$—$MoO_3$, $Al_2O_3$—$WO_3$, $ZrO_2$—ZnO, $ZrO_2$—$TiO_2$, $TiO_2$—MgO, $ZrO_2$—$SnO_2$. Clay-type oxides, such as hydrotalcites, hydroxyapatites, chrysotile and sepiolite, optionally doped with alkali metals and also with metals such as copper, iron or nickel, or rare earth metal oxides doped with alkaline earth metals, such as ($SrO$—$La_2O_3$), may be added to this list of mixed oxides. Other catalysts which may also be suitable for this reaction, such as mixed oxide catalysts of the mixed cobalt and aluminum phosphate type, or silica-alumina doped, for example, with salts of sodium (Na), potassium (K), cesium (Cs), cadmium (Cd), Mg, Ca, Sr, Mn, Zn, Mo, Nb, Pb and/or Si, are also part of this category. They may also be MgO-alumina, MgO—$SiO_2$, rare earth metals in the form of phosphates, tungstates, molybdates, etc. Oxynitrides of phosphorus derivatives, such as mixed oxynitrides of vanadium-aluminum, phosphorus-zirconium, phosphorus-aluminum, vanadium-aluminum-phosphorus or gallium-aluminum-phosphorus, may also be suitable for this reaction.

5) Various "zeolites" exchanged with alkali metal ions (Cs, K, Na, Li).

By way of example of such catalysts, mention may be made of aluminosilicates which are crystalline or amorphous, silicalites, synthetic crystalline zeolites, such as faujasite, ferrierite, ZSM-5, in their acid form or in a form either partially or totally neutralized by elements from Groups 1 to 14 and preferably from Groups 1 and 2 and by Zn and Tl. The zeolites used may have some or all of the aluminum atoms in their structure replaced by trivalent atoms, such as B, Ga, Fe, Cr, V, As, Sb, Bi, Be, and may have some or all of the silicon atoms replaced by tetravalent atoms, such as Ge, Ti, Zr, Hf.

The solid condensation catalysts used in the process according to the invention have a high specific surface, generally of between 40 and 600 $m^2/g$ and preferably between 50 and 200 $m^2/g$.

The acid-base properties of a material may be linked to its composition, for example its crystalline structure, or to surface defects, such as the presence of impurities like alkali metals or alkaline earth metals.

The presence and quantity of basic sites may be determined by any known method, for example by adsorption of an acidic compound, such as $CO_2$ or $SO_2$, and by adsorption energy microcalorimetry measurements. The presence and quantity of acidic sites may for their part be measured by adsorption of a basic compound, such as ammonia, for example.

The measurements of the acidity and basicity of the catalyst are carried out by $SO_2$ adsorption (for basicity) and $NH_3$ adsorption (for acidity) and by adsorption energy microcalorimetry measurements. The usual operating conditions are as follows.

The tests are carried out at 150° C. in a calorimeter (C80 from Setaram) connected to a conventional positive-displacement apparatus fitted with a Barocel capacitance manometer for the pressure measurements. The samples are pretreated by heating under vacuum at 300° C. overnight in a quartz cell. This temperature is reached by increasing the temperature at the rate of 1° C./min. The differential heats of adsorption are measured as a function of the surface coverage by repeated passing of small doses of the respective gases over the sample until an equilibrium pressure of approximately 67 Pa is reached. The sample is then vented over 30 min at the same temperature and a second analogous adsorption series is carried out until an equilibrium pressure of approximately 27 Pa is reached. The difference between the quantities adsorbed between the first and the second adsorption (at 27 Pa) represents the quantity of the respective gases irreversibly adsorbed, which provides an estimate of the number of strong sites respectively acidic or basic.

In some cases, the acidity or basicity of the solid is only revealed if a slight adsorption of water or alcohol is performed beforehand on the solid. In the case of a perfectly dry atmosphere, the surface which is probably dehydrated is less acidic and/or basic. The prior adsorption of water or alcohol may be representative of the operating conditions of the reaction.

The process of the invention comprises two successive phases, oxidation then aldol condensation, which may be carried out in the presence of a single molybdenum-based selective oxidation catalyst. These two phases may then be carried out in a single reactor, or optionally in two reactors in cascade.

In the case in which the reaction system consists of a single reactor, the latter comprises either just one fixed catalytic bed consisting of a single molybdenum-based oxidation catalyst or of a physical mixture of the two catalysts—the molybdenum-based oxidation catalyst and the condensation catalyst—or comprises two superimposed catalytic beds with the first (upstream) being loaded with an oxidation catalyst and the second being loaded with a condensation catalyst. In the variant embodiment with two reactors in the reaction system, the first reactor will serve to simultaneously oxidize the two alcohols, and the second will serve for the cross-condensation of the two aldehydes contained in the outlet effluent from the first reactor and for the dehydration of the aldol formed.

In this reaction system, the reactions are carried out in the gas phase at a temperature of between 200 and 400° C. and preferably between 250 and 350° C., under a pressure of between 1 and 10 bar absolute and preferably between 1 and 5 bar absolute.

The alcohol mixture—methanol and ethanol or methanol and propanol depending on the case—is such that the methanol/ethanol and methanol/propanol molar ratios are between 0.8 and 2, in general between 1 and 2 and preferably between 1.1 and 1.5.

In the case of an excess of one of the reactants, said excess will advantageously be able to be recycled into the reactor in the initial alcohol form or in the form converted into aldehyde.

The rate of introduction of the alcohol mixture into the reaction system is such that the total content of alcohols in the reaction medium is between 4 and 10% and preferably between 6 and 9%, expressed by volume.

The rate of introduction of the oxygen will be such that the oxygen content of the reaction medium will not be higher than 10% by volume.

The remainder of the reaction medium consists of one or more inert gas(es) which represent from 80 to 88% by volume of the reaction medium. The presence of these inert gas(es) is essential to prevent the mixture from being in the explosion range. These inert gases will be, for example, steam, carbon dioxide, nitrogen or a noble gas, such as argon or helium. Nevertheless, as long as the reactor is fitted with rupture disks or other safety devices, it is possible to operate with an oxygen concentration of greater than 10% by volume.

The reactions are carried out with an HSV (hourly space velocity) generally of between 2000 and 40 000 $h^{-1}$ and preferably between 10 000 and 20 000 $h^{-1}$. The HSV is calculated by taking the ratio of the total gas flow rate (in standard liters) divided by the volume of catalyst (bulk density taken at 1 g/ml). In this method, only the active material is taken into account and not the inert solids used to dilute the catalyst.

In a variant embodiment of the process using two successive reactors, it will be possible if appropriate to carry out a partial condensation on the outlet effluent from the first reactor, in order to eliminate a fraction of water before introduction into the condensation reactor, since the water is not very favorable to the aldol reaction. On this occasion, heavy compounds, such as acetic acid, propionic acid, acrylic acid and formic acid, may also be removed, which heavy compounds would certainly be formed, even at trace levels, and which might react in the step of aldol reaction of the effluent coming from the first reactor.

The following examples illustrate the present invention without, however, limiting the scope thereof.

EXAMPLE 1

Synthesis of a Condensation Catalyst

The $Cs/Zr/SiO_2$-type catalyst is prepared from a silica gel in the form of particles of 315 to 500 microns with a purity of 99.9%, a specific surface of 320 $m^2/g$ and a pore volume of 0.9 $cm^3/g$ with a median pore diameter of 9 nm.

The silica is impregnated with a solution of zirconium butoxide in butanol, followed by filtration and drying in a rotary evaporator and then in an oven at 120° C. for 2 hours. The impregnation and drying were repeated 2 more times so as to obtain a deposition of 0.02% by weight (1.2 g of zirconium per 100 mol of silica). The cesium is then itself also impregnated from an aqueous solution of cesium carbonate, followed by drying, to give a cesium content of approximately 4 wt % (calculated as weight of metal). The catalyst is then calcined at 450° C. under air for 3 hours. The specific surface of the catalyst thus prepared is 147 $m^2/g$.

EXAMPLE 2

Synthesis of a Condensation Catalyst

The $Na/SiO_2$ catalyst is prepared by impregnating a large-pore silica gel supplemented with 12 wt % sodium silicate. After impregnation, the solid is dried in a drying oven at 100° C. for 10 h and then calcined in an oven at 500° C. for 3 hours. The specific surface of the catalyst prepared is 122 $m^2/g$.

EXAMPLE 3

Acrolein Synthesis in the Presence of a Catalyst Mixture 200 mg of a mixture of oxidation catalyst (A) from Mapco, MS, of iron molybdate (FeMo) type, and condensation catalyst (B) of $Na/SiO_2$ type (denoted by Na in table 1) or $Cs/Zr/SiO_2$ type (denoted by Zr in table 1), which are prepared as described above, are introduced into a reactor with a 1 cm internal diameter.

The catalyst mixture is subjected to grinding and, after sieving, the fraction of the powder with a particle size of between 80 and 100 µm is selected. This powder is diluted by an equivalent quantity of silicon carbide (SiC) with a particle size of 105 µm. Finally, 500 mg of SiC are added above the catalytic bed thus constituted, to promote the homogeneity and the flow of the reaction stream and the heating.

The injection rate of the gaseous feedstock, preheated to 120° C., is 50 ml/minute, i.e. 3000 ml/h. The alcohol mixture is injected as a liquid into an evaporator in which it comes into contact with the other gases.

The gaseous feedstock mixture has the following composition, according to the tests: 8 or 10% oxygen, equimolar mixture of 4 or 5% ethanol and 4 or 5% methanol and the remainder (80 to 84%) helium (containing 1% Kr as internal standard).

The alcohol mixture is supplied by a pump and passes through an evaporator before joining the gas stream upstream of the reactor.

The reactor is placed in an electrically heated oven. In the following tests, the reaction is carried out at a pressure very slightly greater than atmospheric pressure and at a temperature varying from 250 to 400° C.

The effluents are analyzed by chromatography with an FID (flame ionization detector) and with detection by mass spectrometry.

The results obtained are given in table 1 below.

The product yields are calculated taking into account the number of carbon atoms in the reactants and products.

Thus, the acrolein yield is: 3×(number of moles of acrolein detected)/(moles of entering methanol+2×number of moles of entering ethanol).

Likewise, the acetaldehyde yield is: 2×(number of moles of acetaldehyde detected)/(moles of entering methanol+2×number of moles of entering ethanol), although, chemically speaking, the acetaldehyde was probably obtained only from ethanol.

remainder of the reactor is subsequently filled with silicon carbide to ensure that the reaction gases are preheated and that the gases are well distributed.

The alcohol mixture is supplied by an HPLC pump to the reactor. The liquid stream is mixed with the gas stream (helium-oxygen) at an evaporator maintained at 125° C. to ensure total vaporization of the alcohols. The total flow rate of the gas stream sent to the reactor is then 50 ml/minute, i.e. an estimated hourly space velocity of 15 000 $h^{-1}$.

The effluents from the reactor are cooled and trapped in a condenser which contains a small amount of water and is maintained at 4° C. The non-condensable gases are analyzed in-line by chromatography and the condensed effluents are analyzed separately by chromatography.

The conversion is calculated for the alcohol mixture as being the number of moles of carbon converted divided by the number of moles of carbon entering the reactor. This enables a single parameter to be retained when the methanol/ethanol ratio is varied.

The selectivity is calculated as the number of moles of carbon (in the product in question) divided by the number of moles of carbon having been converted.

TABLE 1

| Test | Cata B mg | Cata A mg | $CH_3OH$ + $CH_3CH_2OH$ (1:1 ratio) % | $O_2$ % | T ° C. | Methanol conversion % | Ethanol conversion % | Acrolein yield % | Acetaldehyde yield % |
|---|---|---|---|---|---|---|---|---|---|
| 1 | Zr 100 | FeMo 100 | 8 | 8 | 325 | 88.5 | 99.5 | 41.1 | 46.3 |
| 2 | Zr 100 | FeMo 100 | 8 | 8 | 350 | 91 | 99.2 | 40.9 | 36.8 |
| 3 | Zr 67 | FeMo 133 | 8 | 8 | 300 | 87.8 | 99.8 | 47.9 | 30.9 |
| 4 | Zr 67 | FeMo 133 | 8 | 8 | 325 | 98.6 | 99.6 | 67.1 | 11.9 |
| 5 | Zr 67 | FeMo 133 | 8 | 8 | 350 | 84 | 96 | 7 | 14.7 |
| 6 | Zr 133 | FeMo 67 | 8 | 8 | 325 | 88.5 | 99.4 | 43.1 | 42.8 |
| 7 | Zr 133 | FeMo 67 | 8 | 8 | 350 | 95.3 | 99.4 | 38.9 | 24.3 |
| 8 | Na 100 | FeMo 100 | 8 | 8 | 300 | 79.6 | 99.7 | 33 | 61.1 |
| 9 | Na 100 | FeMo 100 | 8 | 8 | 325 | 95.3 | 99.5 | 47.7 | 38 |
| 10 | Na 100 | FeMo 100 | 8 | 8 | 350 | 98.6 | 99.8 | 39.9 | 20.3 |
| 11 | Na 100 | FeMo 100 | 10 | 10 | 300 | 79.8 | 99.7 | 43.1 | 41.4 |
| 12 | Na 100 | FeMo 100 | 10 | 10 | 350 | 98.4 | 99.7 | 47.7 | 13.5 |
| 13 | Zr 100 | FeMo 100 | 10 | 10 | 300 | 79.5 | 99.1 | 49.1 | 20.6 |
| 14 | Zr 100 | FeMo 100 | 10 | 10 | 350 | 98.4 | 99.6 | 54.4 | 6.7 |
| 15 | Zr 67 | FeMo 133 | 8 | 8 | 250 | 38.6 | 83.5 | 6.4 | 43.5 |
| 16 | Zr 100 | FeMo 100 | 8 | 8 | 400 | 75.1 | 99 | 18.2 | 40.8 |

EXAMPLE 4

Acrolein Synthesis in the Presence of an Oxidation Catalyst 200 mg of iron molybdate catalyst mixed with an identical volume of silicon carbide with a particle size of 100-125 microns are charged to a glass fixed bed reactor 12 mm in internal diameter placed in a tubular electric oven. The The reactor is supplied with a methanol/ethanol mixture in a ratio of 1.2, with an alcohol total partial pressure of 7.7% and an oxygen partial pressure of 7.8% for a total pressure of 1 atmosphere (absolute).

The predominant products detected are acrolein and acetaldehyde. The conversion of methanol and ethanol at 325° C. is total, and the selectivity for acrolein is 48%. Acrolein was produced in the presence of the single iron molybdate catalyst.

EXAMPLE 5

The preceding example 4 is reproduced with a methanol/ethanol ratio of 0.8 and the same alcohol total partial pressure. The selectivity for acrolein is then 57%, for a 92% conversion of the alcohols.

EXAMPLE 6

The preceding example 4 is reproduced with a methanol/ethanol ratio of 1.2 and with 3 times the weight of catalyst (600 mg). The conversion of the alcohols is still 100%, but the selectivity for acrolein decreases to 40% while the selectivity for acetaldehyde increases to 22%.

EXAMPLE 7

The reaction is carried out as in the preceding example 4 but using, as oxidation catalyst, the catalyst ACF-4 from Nippon Shokubai, which is a bismuth molybdate-type catalyst notably used for the oxidation of propylene to acrolein.

The reaction is carried out at 300° C. with 250 mg of catalyst. A methanol/ethanol ratio of 1.3, a partial pressure of the alcohol mixture of 8% and an oxygen partial pressure of 10% are employed.

The acrolein yield is 18%.

The invention claimed is:

1. A process for the direct synthesis of an unsaturated aldehyde of formula $CH_2=C(R)-CHO$, wherein R represents H or $CH_3$, from a feedstock containing an alcohol mixture comprising methanol and a second alcohol of formula $R-CH_2-CH_2OH$, the process comprising:
    introducing the alcohol mixture, oxygen and an unreactive diluent gas into a reaction system comprising a solid selective oxidation catalyst chosen from molybdenum-based catalysts and optionally a solid aldol condensation catalyst, wherein said reaction system is operated in the gas phase at a temperature of between 200 and 400° C. and under a pressure of between 1 and 10 bar absolute, and wherein the alcohol mixture and the oxygen each represent at most 10% of a total volume of a reaction mixture in the reaction system, and
    recovering a gaseous effluent comprising the formed unsaturated aldehyde and water, coproduced by the reaction, at an outlet of the reaction system.
2. The process as claimed in claim 1, wherein the oxidation catalyst is represented by the general formula:

$$A_aX_bMo_cZ_dO_e \qquad (I)$$

wherein:
    A is at least one cation selected from the group consisting of the elements of Groups 1 to 16 of the Periodic Table of the Elements and the lanthanides,
    X is P or Si,
    Z is at least one element selected from the group consisting of W, Ti, Zr, V, Nb, Ta, Cr, Mn, Fe, Co, Ni, Cu, Zn, Ga, In, Tl, Sn, Ag, As, Ge, B, Bi, La, Ba, Sb, Te, Ce and Pb,
    O is oxygen,
    a, b, c and d are indices consisting of integers or decimals corresponding to the following ranges:
    $0 \leq a \leq 9$
    $0 \leq b \leq 2$
    $0 < c \leq 12$
    $0 \leq d \leq 12$
    such that $a+b+d>0$,
    and e is a number determined by the total degree of oxidation of the elements.
3. The process as claimed in claim 2, wherein the oxidation catalyst is an iron molybdate corresponding to the general formula (I), with the value of the indices a and b being 0 and the value of the index d not being 0.
4. The process as claimed in claim 1, wherein the condensation catalyst is selected from the group consisting of alkali metal hydroxides LiOH, NaOH, KOH, or CsOH deposited on a silica or alumina support; alkali metals and alkaline earth metals dispersed on silica, alumina, magnesia, charcoal or potassium carbonate; $LiCO_3$ deposited on silica; and t-BuOK deposited on xonotlite.
5. The process as claimed in claim 1, wherein the condensation catalyst is selected from sodium silicate deposited on silica or on aluminosilicate and further comprising a metal promoter and cesium deposited on silica grafted with or doped by a zirconium compound.
6. The process as claimed in claim 1, wherein the condensation catalyst is selected from the group consisting of
    i) $SiO_2-MgO$, $SiO_2-CaO$, $SiO_2-SrO$, $SiO_2-BaO$, $SiO_2-SnO$, $SiO_2-ZnO$, $SiO_2-Al_2O_3$, $SiO_2-ThO_2$, $SiO_2-TiO_2$, $SiO_2-ZrO_2$, $SiO_2-MoO_3$, $SiO_2-WO_3$, $Al_2O_3-MgO$, $Al_2O_3-ThO_2$, $Al_2O_3-TiO_2$, $Al_2O_3-ZrO_2$, $Al_2O_3-MoO_3$, $Al_2O_3-WO_3$, $ZrO_2-ZnO$, $ZrO_2-TiO_2$, $TiO_2-MgO$, or $ZrO_2-SnO_2$,
    ii) hydrotalcites, hydroxyapatites, chrysolite and sepiolite, optionally doped with alkali metals and other metals,
    iii) rare earth metal oxides doped with alkaline earth metals,
    iv) mixed oxides of the mixed cobalt and aluminum phosphate type,
    v) silicas-aluminas doped with salts of Na, K, Cs, Cd, Mg, Ca, Sr, Mn, Zn, Mo, Nb, Pb and/or Si,
    vi) MgO-alumina or $MgO-SiO_2$,
    vii) rare earth metals in the form of phosphates, tungstates or molybdates, and
    viii) mixed oxynitrides of vanadium-aluminum, phosphorus-zirconium, phosphorus-aluminum, vanadium-aluminum-phosphorus or gallium-aluminum-phosphorus.
7. The process as claimed in claim 1, wherein the process is carried out at a temperature of between 250 and 350° C. under a pressure of between 1 and 5 bar absolute.
8. The process as claimed in claim 1, wherein the rate of introduction of the alcohol mixture into the reaction system is such that the total content of alcohols in the reaction medium is between 4 and 10%, expressed by volume.
9. The process as claimed in claim 1, wherein for the alcohol mixture, the methanol/second alcohol molar ratio is between 0.8 and 2.
10. The process as claimed in claim 1, wherein the reactions are carried out with an HSV of between 2000 and 40 000 $h^{-1}$.
11. The process as claimed in claim 1, wherein the reactions are carried out in a single reactor with a catalytic bed comprising a single molybdenum-based oxidation catalyst or a physical mixture of a molybdenum-based oxidation catalyst and a condensation catalyst.
12. The process as claimed in claim 1, wherein the reaction system contains both a molybdenum-based oxidation catalyst and a solid aldol condensation catalyst.
13. The process as claimed in claim 12, wherein the reactions are carried out in a single reactor with two superimposed catalytic beds, the oxidation catalytic bed being placed upstream.

14. The process as claimed in claim 12, wherein the reaction system comprises two reactors, the first reactor serving to simultaneously oxidize the two alcohols, and the second reactor serving for the cross-condensation of the two aldehydes contained in the outlet effluent from the first reactor and for the dehydration of the aldol formed.

* * * * *